United States Patent
Ashton et al.

(10) Patent No.: US 9,700,465 B2
(45) Date of Patent: Jul. 11, 2017

(54) DISPOSABLE ABSORBENT ARTICLE WITH ELASTICALLY CONTRACTIBLE CUFFS FOR BETTER CONTAINMENT OF LIQUID EXUDATES

(75) Inventors: Gregory Ashton, Cincinnati, OH (US); Masaharu Nishikawa, Cincinatti, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1430 days.

(21) Appl. No.: 12/476,271

(22) Filed: Jun. 2, 2009

(65) Prior Publication Data
US 2010/0305532 A1    Dec. 2, 2010

(51) Int. Cl.
| A61F 13/15 | (2006.01) |
| A61F 13/20 | (2006.01) |
| A61F 13/532 | (2006.01) |
| A61F 13/494 | (2006.01) |

(52) U.S. Cl.
CPC ...... *A61F 13/5323* (2013.01); *A61F 13/4942* (2013.01); *Y10T 156/1051* (2015.01)

(58) Field of Classification Search
USPC ............. 604/385.23–385.3, 385.01, 385.101
See application file for complete search history.

(56) References Cited

U.S. PATENT DOCUMENTS

| 3,848,594 A | 11/1974 | Buell |
| 3,860,003 A | 1/1975 | Buell |
| 4,081,301 A | 3/1978 | Buell |
| 4,253,461 A | 3/1981 | Strickland et al. |
| 4,610,678 A | 9/1986 | Weisman et al. |
| 4,636,207 A | 1/1987 | Buell |
| 4,662,875 A | 5/1987 | Hirotsu et al. |
| 4,743,246 A * | 5/1988 | Lawson .................. 604/385.27 |
| 4,834,735 A | 5/1989 | Alemany et al. |
| 4,846,815 A | 7/1989 | Scripps |
| 4,869,724 A | 9/1989 | Scripps |
| 4,888,231 A | 12/1989 | Angstadt |
| 4,940,464 A | 7/1990 | VanGompel et al. |
| 5,021,051 A * | 6/1991 | Hiuke ..................... 604/385.27 |

(Continued)

FOREIGN PATENT DOCUMENTS

| EP | 0 149 880 A2 | 7/1985 |
| JP | 07-184947 A | 7/1995 |

(Continued)

OTHER PUBLICATIONS

International Search Report, PCT/US2009/046205, mailed May 10, 2009, 18 pages.

*Primary Examiner* — Michele M Kidwell
(74) *Attorney, Agent, or Firm* — William E. Gallagher; Andrew J. Mueller

(57) ABSTRACT

A disposable absorbent article includes an absorbent core, a liquid permeable topsheet, a liquid impermeable backsheet, and a pair of elastically contractible cuffs, each of which is constructed of a continuous cuff material and has a standing cuff portion which includes one or more elastic members. Each elastically contractible cuff may be secured the topsheet about a longitudinal edge of the topsheet by an assembly bond, with a standing cuff portion laterally offset away from a longitudinal edge of the absorbent core and with one or more elastic members located outboard of the assembly bond.

17 Claims, 11 Drawing Sheets

(56) References Cited

U.S. PATENT DOCUMENTS

| | | |
|---|---|---|
| 5,037,416 A | 8/1991 | Allen et al. |
| 5,092,861 A | 3/1992 | Nomura et al. |
| 5,137,537 A | 8/1992 | Herron et al. |
| 5,151,092 A | 9/1992 | Buell et al. |
| 5,242,436 A | 9/1993 | Weil et al. |
| 5,246,433 A | 9/1993 | Hasse et al. |
| 5,260,345 A | 11/1993 | DesMarais et al. |
| 5,269,775 A | 12/1993 | Freeland et al. |
| 5,387,207 A | 2/1995 | Dyer et al. |
| 5,397,316 A | 3/1995 | LaVon et al. |
| 5,554,145 A | 9/1996 | Roe et al. |
| 5,569,234 A | 10/1996 | Buell et al. |
| 5,571,096 A | 11/1996 | Dobrin et al. |
| 5,591,155 A | 1/1997 | Nishikawa et al. |
| 5,625,222 A | 4/1997 | Yoneda et al. |
| 5,827,387 A | 10/1998 | Reynolds et al. |
| 5,897,545 A | 4/1999 | Kline et al. |
| 5,957,908 A | 9/1999 | Kline et al. |
| 5,993,433 A * | 11/1999 | St. Louis et al. ........ 604/385.27 |
| 6,004,306 A | 12/1999 | Robles et al. |
| 6,120,487 A | 9/2000 | Ashton |
| 6,120,489 A | 9/2000 | Johnson et al. |
| 6,123,694 A | 9/2000 | Pieniak et al. |
| 6,126,648 A | 10/2000 | Keck et al. |
| 6,645,569 B2 | 11/2003 | Cramer et al. |
| 6,706,029 B1 | 3/2004 | Suzuki et al. |
| 6,863,933 B2 | 3/2005 | Cramer et al. |
| 7,112,621 B2 | 9/2006 | Rohrbaugh et al. |
| 7,118,557 B2 * | 10/2006 | Minato et al. ........... 604/385.27 |
| 2003/0105190 A1 | 6/2003 | Diehl et al. |
| 2003/0120247 A1 | 6/2003 | Miyamoto |
| 2003/0148684 A1 | 8/2003 | Cramer et al. |
| 2003/0233082 A1 | 12/2003 | Kline et al. |
| 2004/0002690 A1 | 1/2004 | Miyamoto |
| 2004/0092902 A1 | 5/2004 | Hoffman et al. |
| 2005/0008839 A1 | 1/2005 | Cramer et al. |
| 2005/0131375 A1 | 6/2005 | Sasaki et al. |
| 2005/0159720 A1 | 7/2005 | Gentilcore et al. |
| 2005/0177123 A1 | 8/2005 | Catalan |
| 2005/0234411 A1 | 10/2005 | Ashton et al. |
| 2006/0151091 A1 | 7/2006 | Komatsu |
| 2007/0118087 A1 | 5/2007 | Flohr et al. |

FOREIGN PATENT DOCUMENTS

| | | |
|---|---|---|
| JP | 2000-238161 A | 9/2000 |
| WO | WO 95/16746 A1 | 6/1995 |
| WO | WO 99/13813 | 3/1999 |
| WO | WO 02/064877 A2 | 8/2002 |
| WO | WO 2006/062258 A2 | 6/2006 |

\* cited by examiner

DISPOSABLE ABSORBENT ARTICLE WITH ELASTICALLY CONTRACTIBLE CUFFS FOR BETTER CONTAINMENT OF LIQUID EXUDATES

FIELD OF THE INVENTION

The present invention generally relates to an absorbent article, and more particularly to a disposable absorbent garment, such as a taped diaper or training pant.

BACKGROUND OF THE INVENTION

Absorbent articles, such as disposable diapers, training pants, and adult incontinence undergarments, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Contemporary absorbent articles often may include a topsheet, a backsheet, an absorbent core, a barrier cuff, and a gasketing cuff. The gasketing cuff is intended to prevent wicking and overflow from the fluid laden article to clothing contacting the edges of the article, in that the gasketing cuff presents a fluid impermeable barrier between the edge of the article and the contacting clothing. In addition, it provides a gasketing action about the legs of the wearer. The barrier cuff is intended to inhibit loose fecal matter or gushes of urine or liquids from soiling the wearer's clothing. The barrier cuff desirably restrains the free flow of this material and provides a structure to hold such material within the article.

One common mode of failure for such absorbent article products occurs when body exudates leak out of product through gaps between the article and the wearer's torso or legs when the liquid exudate is not immediately absorbed within the article. Such leakage problems may be more likely to occur when the wearer is prone on his back. The failure mode may become more prevalent when an absorbent article is made better fitting and with a less bulky absorbent core, where the absorbent core cannot absorb the liquid exudate as rapidly as released by the wearer into the article. Accordingly, it would be desirable to increase the liquid volume holding capacity of the absorbent article to retain the free liquid exudate before and during absorption by the absorbent core. In addition, it would be desirable to maintain or enhance the liquid volume holding capacity of a thin, flexible absorbent article with minimum bulk and/or a narrow crotch for improved comfort.

SUMMARY OF THE INVENTION

The present invention addresses one or more of the foregoing technical problems and provides a disposable absorbent article which may comprise an absorbent core having a garment surface and an opposed body surface, which surfaces meet along a pair of longitudinal edges and a pair of end edges; a liquid permeable topsheet positioned adjacent the body surface of the absorbent core and having a pair of opposed longitudinal edges; a liquid impermeable backsheet positioned adjacent the garment surface of the absorbent core; and a pair of elastically contractible cuffs, each of which is constructed of a continuous cuff material and has a standing cuff portion which comprises one or more elastic members, wherein each elastically contractible cuff is secured about one of the longitudinal edges of the topsheet by an assembly bond, with the standing cuff portion being laterally offset away from the longitudinal edge of the absorbent core and with the one or more elastic members being located outboard of the assembly bond. The elastically contractible cuffs may be attached to the topsheet. It may alternatively or additionally be attached to the backsheet or another suitable surface. In one embodiment, the elastically contractible cuffs may be mechanically bonded to the topsheet and glued to the backsheet.

According to another aspect of this invention, a method is provided for constructing a disposable absorbent article having an outboard cuff. The method includes the steps of a) adhering one or more elastic members onto a layer of a continuous cuff material; b) folding the continuous cuff material onto itself with the elastic members being located between at least two layers of the continuous cuff material to form a first elastically contractible cuff; c) repeating steps a) and b) to form a second elastically contractible cuff; d) folding each of the first and second elastically contractible cuffs over onto itself; and e) securing the first folded elastically contractible cuff about a first longitudinal edge of a liquid permeable topsheet by a first assembly bond and securing the second folded elastically contractible cuff about a second longitudinal edge of the topsheet by a second assembly bond, such that the elastic members of each of the first and second cuffs are located outboard of the first and second assembly bonds, to form a cuff/topsheet composite. In one embodiment, the first and second cuffs are mechanically bonded to the topsheet.

Other features and advantages of the invention may be apparent from reading the following detailed description, drawings, and claims.

DETAILED DESCRIPTION OF THE INVENTION

Figure 1:
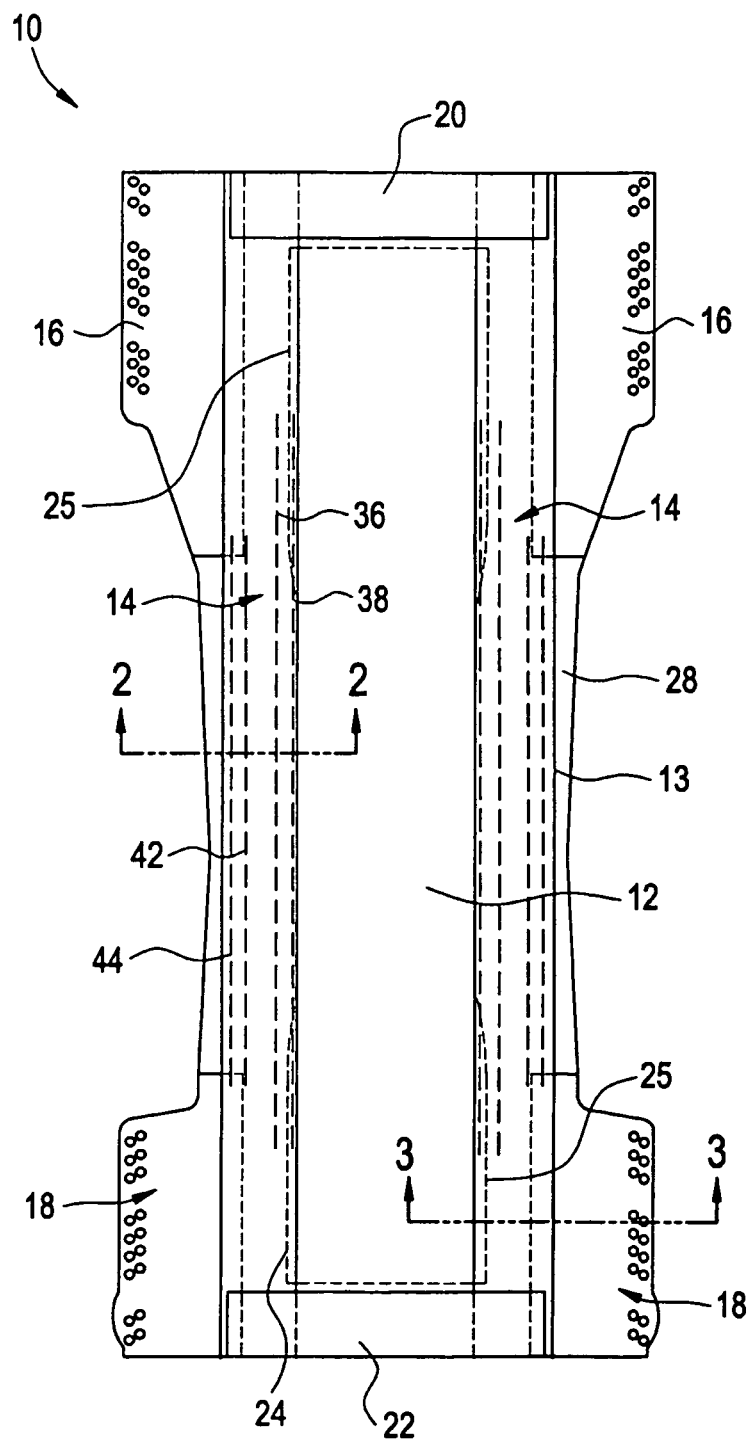
FIG. 1 is a plan view of a diaper in accordance with an embodiment of the present invention.

As summarized above, the present invention may encompass a disposable absorbent article, such as a diaper, and a method for constructing such a diaper having an outboard cuff and with the elastic members of the cuff being located outboard of the assembly bond. Advantageously, this provides increased volume for retaining liquid exudate until the exudate can be acquired by the absorbent core and/or an acquisition system of the absorbent core. By having a standing cuff portion laterally offset away from the longitudinal edge of the absorbent core, the Effective Cuff Height advantageously may be increased without increasing the height of the standing cuff portion. It also permits an effective cuff height over whole length of the absorbent article, which can enhance leakage prevention, particular overnight leakage and leakage when the wearer is in the prone on back position. The combination of a core substantially cellulose free and an outboard cuff advantageously may provide the disposable absorbent article with improved softness, flexibility, and conformity to a wearer's body for greater comfort without increasing the likelihood of leakage from the disposable absorbent article. In one embodiment of the invention, the standing cuff portion is folded so that the distal edge of the standing cuff portion is pointing outboard of the absorbent article.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein the first substrate and second substrate are separated by a multiplicity of superabsorbent particles. The boundary of the absorbent particulate polymer material area is defined by the perimeter of the overlapping circles. There may be some extraneous superabsorbent particles outside of this perimeter between the first substrate and second substrate.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Elastic", "elastically extensible", and "elasticized" refer herein to the property of a material and/or an element of a diaper or other disposable absorbent article whereby the material and/or the element can be elongated to at least 150% of its original unstretched length without rupture or catastrophic failure upon the application of tensioning force and will substantially return to its original length or near its original length after the tension is released.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate and second substrate are separated by a multiplicity of superabsorbent particles. It is recognized that there may be minor incidental contact areas between the first substrate and second substrate within the absorbent particulate polymer material area. Incidental contact areas between the first substrate and second substrate may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

FIG. 1 is a plan view of a diaper 10 according to a certain embodiment of the present invention. The diaper 10 is shown in its flat out, uncontracted state (i.e., without elastic induced contraction). The diaper 10 is depicted in FIG. 1 with its longitudinal axis vertically oriented on the drawing, and its transverse axis horizontally oriented on the drawing. A portion of the diaper 10 that contacts a wearer is facing the viewer of in FIG. 1. The diaper 10 may include a pair of elastically contractible cuffs 14 and an absorbent core 24 encased between a liquid permeable topsheet 12 and a liquid impermeable backsheet 28. Each elastically contractible cuff 14 includes elastic members 36, 38, 42, and 44.

The absorbent core 24 may have a garment surface and an opposed body surface, which surfaces meet along a pair of longitudinal edges 25 and a pair of end edges. The liquid permeable topsheet 12 may be positioned adjacent the body surface of the absorbent core 24 and may have a pair of opposed longitudinal edges 13. The liquid impermeable backsheet 28 may be positioned adjacent the garment surface of the absorbent core 24.

The diaper 10 may also include back side panel assemblies 16 and front side panel assemblies 18. The diaper 10 may also include back waistband 20 at a first end and a front waistband 22 at the opposite, second end. An intermediate portion of the diaper 10 may be configured as a crotch region, which extends longitudinally between the front and back waist bands 20 and 22. The waist bands 20 and 22 may include elastic elements such that they gather about the waist of the wearer to provide improved fit and containment. The crotch region is that portion of the diaper 10 which, when the diaper 10 is worn, is generally positioned between the wearer's legs. The diaper 10 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the topsheet 12, the backsheet 28, and the absorbent core 24 may be assembled in a variety of well-known configurations, exemplary diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 12 in FIG. 1 may be fully or partially elasticized or may be foreshortened to provide a void space between the topsheet 12 and the absorbent core 24. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 28 may be joined with the topsheet 12. The backsheet 28 may prevent the exudates absorbed by the absorbent core 24 and contained within the diaper 10 from soiling other external articles that may contact the diaper 10, such as bed sheets and undergarments. In certain embodiments, the backsheet 28 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing exudates from passing through the backsheet 28. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

Figure 2:
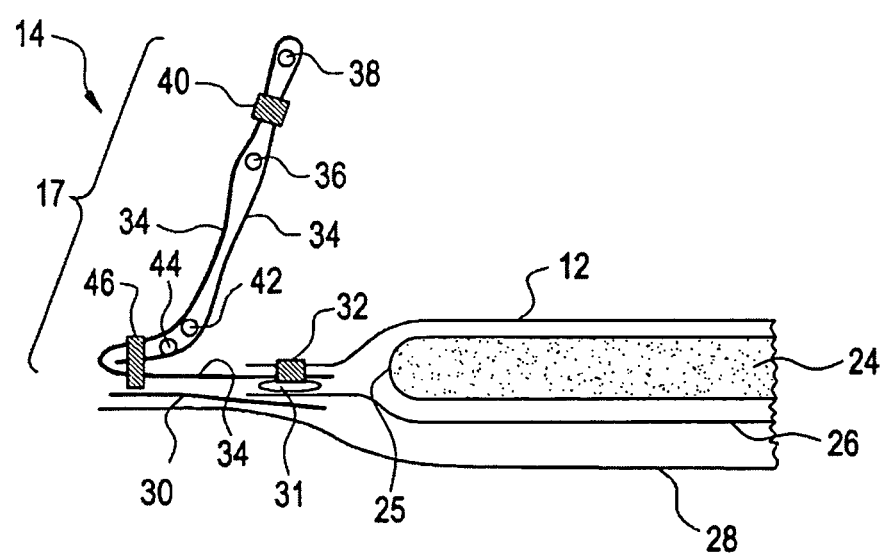
FIG. 2 is a cross-sectional view in a crotch region of a diaper in accordance with an embodiment of the present invention.

FIG. 2 shows a cross section of FIG. 1 taken along the sectional line 2-2 of FIG. 1. FIG. 2 illustrates the construction of the elastically contractible cuff 14 on the left side of the diaper 10 shown in FIG. 1, in the crotch region of the diaper 10. The elastically contractible cuff 14 may be constructed of a continuous cuff material 34 and may have a standing cuff portion 17 which comprises elastic members 36, 38, 42, and 44. In one embodiment of the invention, the standing cuff portion is folded so that the distal edge of the standing cuff portion is pointing outboard of the absorbent article. In one embodiment, one or more of the elastic members are fixed to the continuous cuff material by intermittent adhesive zones where the adhesive zones comprise at least two discrete sections along the length of the elastic member. In one embodiment, at least a portion of the contractible cuff is constructed of a single layer of a continuous cuff material. In one embodiment, the elastic members 36, 38, 42, and 44 may be a continuously bonded or a drawstring execution. Different numbers of elastic members may be used, such as one, two, three, four, five, six, or more, for each elastically contractible cuff 14. Each elastically contractible cuff 14 may be secured to the topsheet 12 about one of said longitudinal edges 13 of the topsheet 12 by a continuous absorbent assembly bond 32. The standing cuff portion 17 may be laterally offset away from the longitudinal edge 25 of the absorbent core 24. In a certain embodiment, the elastic members 36, 38, 42, 44 are enveloped in the continuous cuff material 34 and all are located outboard of the assembly bond 32.

In contrast to the construction of several conventional diaper designs, the continuous cuff material 34 is, in one embodiment, not part of the backsheet 28. In addition, the diaper 10 having elastically contractible cuff 14 does not, in one embodiment, include any other elasticized cuff around the leg.

The elastic members 36, 38, 42, 44 may be elastic strands having a cross section of 0.18 mm by 1.5 mm and made from natural rubber as available from Easthampton Rubber Company of Stewart, Va., under the trademark L-1900 Rubber Compound. Other suitable elastics can be made from natural rubber, such as elastic tape sold under the trademark Fulflex 9411 by Fulflex Company of Middletown, R.I. The elastic members 36, 38, 42, 44 may also comprise any heat shrinkable elastic material as is well known in the art. Other suitable elastic materials may comprise a wide variety of materials known in the art, such as but not limited to elastomeric films, polyurethane films, elastomeric foams, formed elastic scrim and synthetic elastomers (e.g., Lycra™). In addition, elastic members 36, 38, 42, 44 may take a multitude of configurations. For example, the width may be varied; a single strand or several parallel or non-parallel strands of elastic material may be used; or a variety of shaped may be used including rectilinear and curvilinear.

The elastic members 36, 38, 42, 44 may be operatively associated with their respective cuff by securing it to/within the continuous cuff material with an elastic attachment element (not shown). The elastic attachment element should be flexible and of sufficient adhesiveness to hold elastic members 36, 38, 42, 44 in their stretched condition. The elastic members 36, 38, 42, 44 having a first and second end, may be secured to their respective cuff only near their ends or along their entire length. The elastic attachment element may be glue beads made of hot melt adhesive such as marketed by Findley Adhesives Incorporated, Elmgrove, Wis., as Findley Adhesives 581. Alternatively, the elastic attachment element may take the form of an ultrasonic bond or heat/pressure seal. A more detailed description of the manner in which the elastic attachment element may be positioned and secured to their respective cuff can be found in U.S. Pat. No. 4,081,301, issued to Buell Mar. 28, 1978, and in U.S. Pat. No. 4,253,461, issued to Strickland and Visscher Mar. 3, 1981.

As shown in FIG. 2, the diaper may include a backsheet inner layer 26 with the (outer layer) backsheet 28. The backsheet inner layer may be made of a substantially impermeable film, such as a polymer film. An adhesive 30 or other suitable material or method may be used to join layers 26 and 28 together. A variety of backsheet configurations are contemplated.

The assembly bond 32 may extend substantially the entire longitudinal length of the diaper 10. The assembly bond 32 may be adhesive, ultrasonic bonding, compression bonding, thermal bonding, combinations thereof, and any other suitable bonding means known in the art which is appropriate for the specific materials employed. In addition, an adhesive bead 31 having liquid impermeability properties may be applied between the topsheet 12 and backsheet 28 (or more specifically as shown in FIG. 2, backsheet inner layer 26) to provide improved barrier properties. The adhesive bead 31 may be located juxtaposed to assembly bond 32; however, so long as adhesive bead 31 helps to provide a containment of exudates, then its actual location is may be varied.

As used herein, the term "continuous cuff material" means a cuff material that is continuous along a path beginning from the assembly bond 32, continuing around the free edge of the cuff, and ending at the cuff fold bond 46, such that the cuff 14 is substantially constructed of two or more layers of the materials over the length of the standing cuff portion 17.

In one embodiment, the continuous cuff material 34 may be constructed of a lesser-water-permeable material (e.g., a spunbound material which is inexpensive) with a more-water-permeable material (e.g., meltblown material which is more expensive) placed inside said lesser-water-permeable material. The continuous cuff material 34 may be constructed of a spunbound-meltblown laminate. In yet another embodiment, the continuous cuff material 34 may be constructed of a series of various materials so long as they are continuous. The continuous cuff material 34 may be treated to increase its hydrophobicity. Such hydrophobic treatments include, but are not limited to, the application of hydrophobic surface coating as described in U.S. Pat. Publication No. 2005/0177123 A1, entitled "Hydrophobic Surface Coated Absorbent Articles And Associated Methods", published Aug. 11, 2005) and flouro-treatment as described in U.S. Pat. Publication No. 2004/0092902 A1, entitled "Disposable Absorbent Article with Masking Topsheet", published May 13, 2004. The elastically contractible cuff 14 may be connected to diaper 10 by way of the assembly bond 32 and/or the adhesive 31.

The elastically contractible cuff 14 may include one or more cuff folds, so as to more readily conform to the wearer's legs and waist. FIG. 2 also shows that the elastically contractible cuff 14 may include a cuff fold bond 46 and cuff end bond 40. These bonds 40, 46 desirably may be continuous along the length of the diaper 10, to minimize potential leakage points, and may be adhesive, ultrasonic bonding, compression bonding, thermal bonding, combinations thereof, or other bonding means known in the art which are suitable for the specific materials employed.

Figure 3:
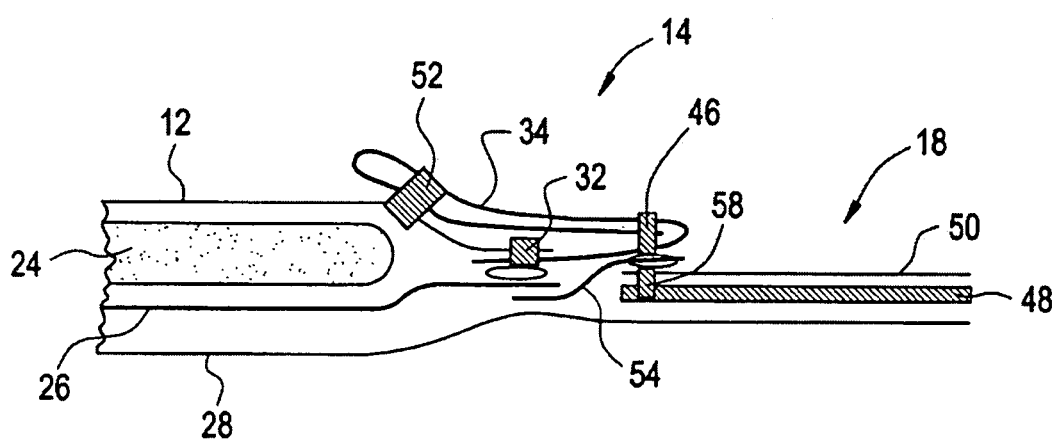
FIG. 3 is a cross-sectional view in an end region of a diaper in accordance with an embodiment of the present invention.

FIG. 3 shows a cross section of FIG. 1 taken along the sectional line 3-3 of FIG. 1. FIG. 3 illustrates the construction of the elastically contractible cuff 14 on the right side of the diaper 10 shown in FIG. 1, and the construction in the (front) end region of the diaper 10. At this end region of the diaper 10, the standing cuff portion may be bonded to the topsheet 12 with tackdown bond 52.

As best seen in FIG. 3, the side panel assembly 18 may include a side panel 48 and a side panel cover 50. The side panel 48 may be elastic and positioned between the side panel cover 50 and the backsheet 28. A bond 58, a sprayed adhesive 54, and/or any other suitable material or method, may be used to join these components together and to the continuous cuff material 34 about the continuous cuff fold bond 46.

Figure 4:
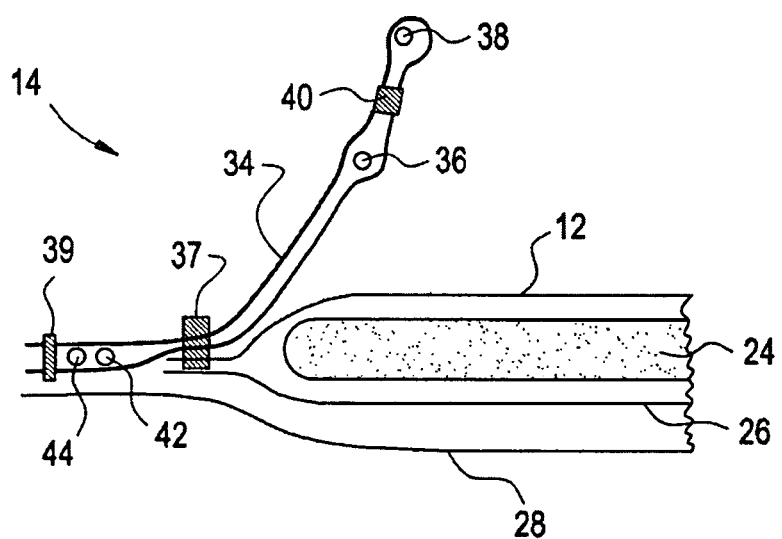
FIG. 4 is a cross-sectional view in a crotch region of a prior art embodiment of a diaper.
Figure 5:
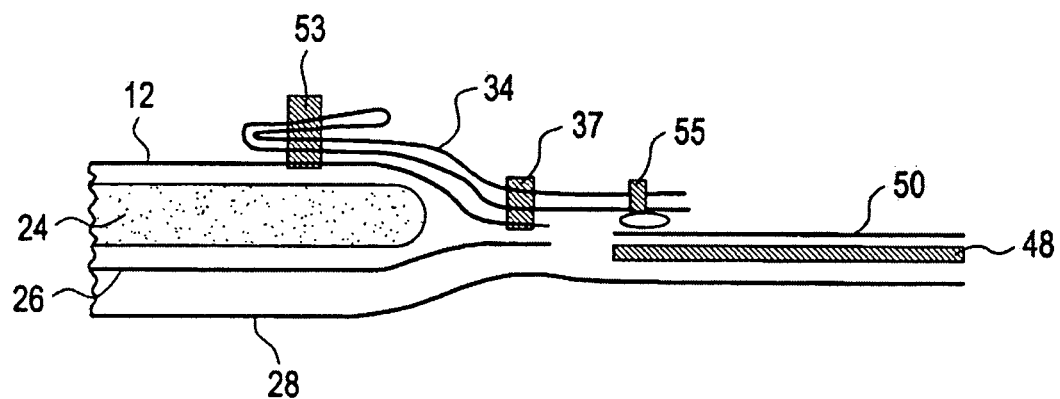
FIG. 5 is a cross-sectional view in an end region of a prior art embodiment of a diaper.

One can see how the structure of the elastically contractible cuff 14 and the diaper 10 of the present invention shown in FIG. 2 and FIG. 3 differ from a conventional prior art embodiment, which is illustrated in FIG. 4 and FIG. 5. These figures show that an assembly bond 37 is disposed in an intermediate position in the continuous cuff material 34 (e.g., intermediate between a cuff end bond 39 and a cuff end bond 40, or between tackdown bond 53 and cuff end bond 55) such that the standing cuff portion is directed toward, and not offset from, the longitudinal edge of the absorbent core, and the elastic members 36, 38 of the standing cuff portion are located inboard, rather than outboard, of the assembly bond 37. By moving the cuff outboard, the diaper advantageously is provided with a structure with greater volume between the cuffs, effectively yielding a bigger "bucket" for containing the liquid exudate until it can be acquired by the absorbent core.

Figure 6:
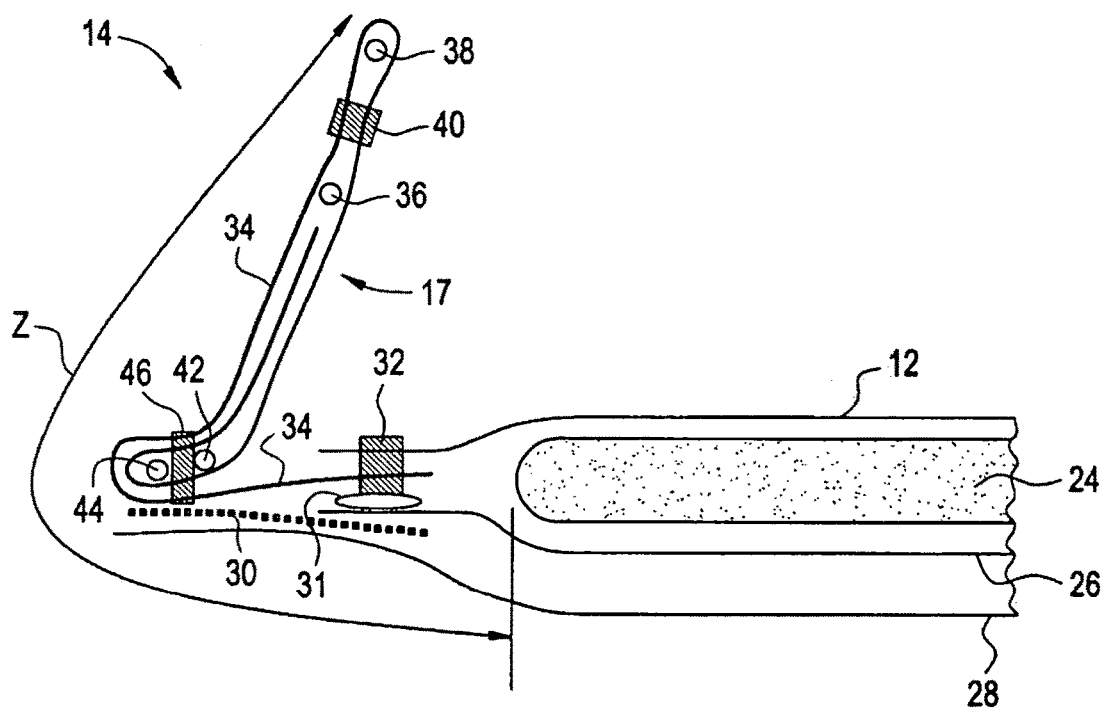
FIG. 6 is a cross-sectional view in a crotch region of a diaper in accordance with another embodiment of the present invention.

FIG. 6 shows an alternative structure for the elastically contractible cuff 14 of diaper 10. In this embodiment, an extra layer of the continuous cuff material may be provided through part of the standing cuff 17, yielding a cuff having a three-layer structure. This may be achieved by including an extra fold of the continuous cuff material at cuff fold bond 46. The extra layer may improve the barrier properties of the leg cuff, for better containment of liquid exudate, as well as retarding migration of surfactant for improved leakage resistance.

FIG. 6 also illustrated the Effective Cuff Height, Z, is measured from the longitudinal edge of the absorbent core 24 to the end of the distal end of the standing cuff portion 17 of the elastically contractible cuff 14. The outboard cuff design of the present invention may enable less cuff material to be used to achieve the same Effective Cuff Height as compared to a conventional pant diaper. Alternatively, as shown in FIG. 2, the actual cuff height, e.g., from cuff fold bond 46 to the opposing end of the standing cuff portion 17, can be increased, yet use the same amount of continuous cuff material as compared to a conventional pant diaper.

Figure 7A:
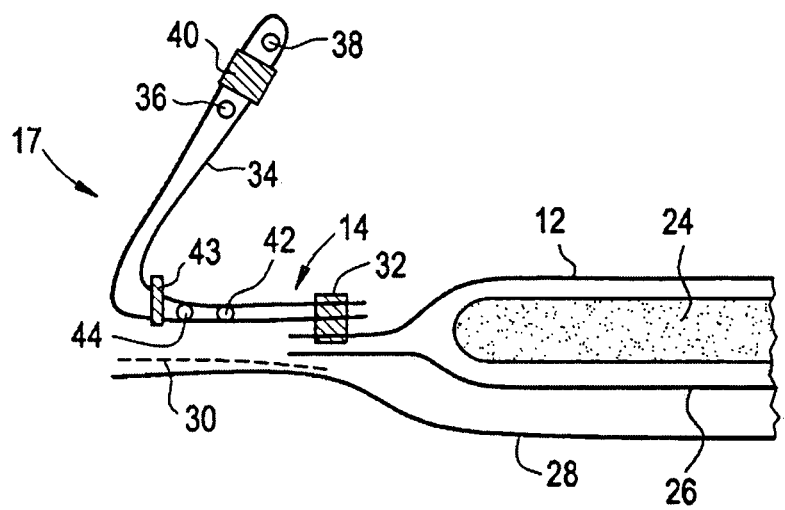
FIGS. 7A-B are cross-sectional views in a crotch region and end region, respectively, of a diaper in accordance with another embodiment of the present invention.
Figure 7B:
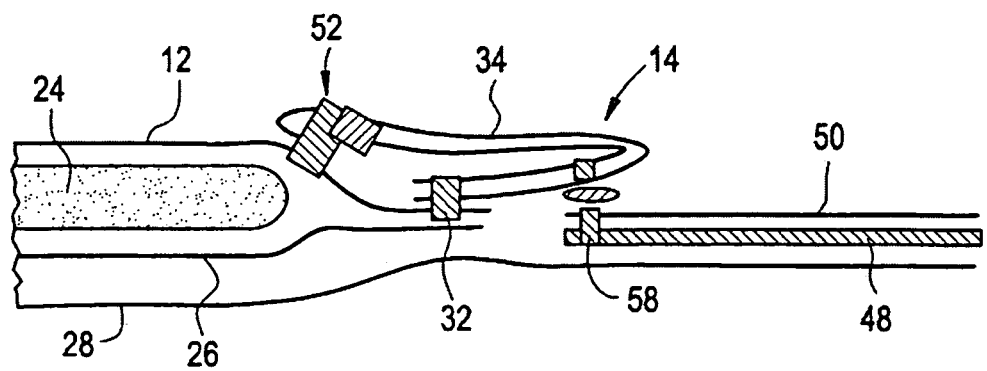
Figure 8A:
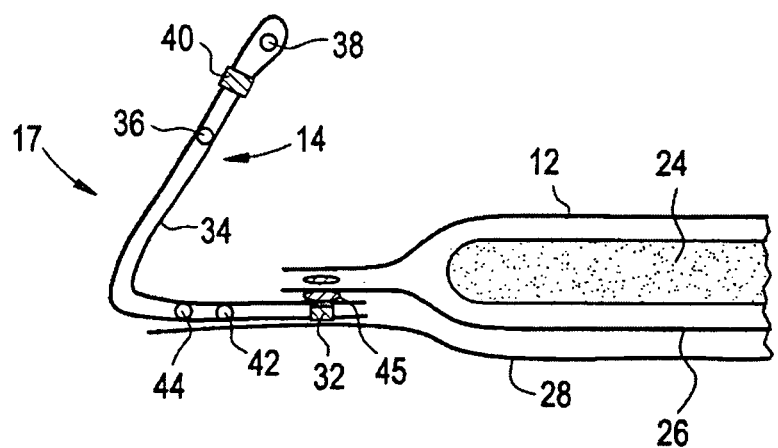
FIGS. 8A-B are cross-sectional views in a crotch region an end region, respectively, of a diaper in accordance with still another embodiment of the present invention.
Figure 8B:
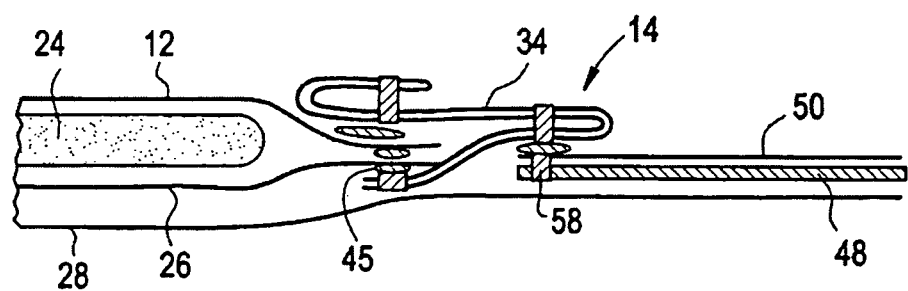

Alternative embodiments of attaching the elastically contractible cuffs 14 about the longitudinal edges of the topsheet 12 are shown in FIGS. 7-8. In FIGS. 7A-B, the cuffs 14 are mechanically bonded to the topsheet 12 by an absorbent assembly bond 32 and secured to the backsheet 28 by an adhesive 30. The cuffs 14 are formed of a continuous cuff material 34 with cuff end bond 40 (hem bond) and continuous bond 43, and with hem elastic 38 and drawstring elastic 36. FIG. 7A shows standing cuff portion 17 laterally offset from the longitudinal edge of the absorbent core 24 with elastic members 42, 44, 36, 38 located outboard of the assembly bond 32. FIG. 7B shows the construction at the side panel 48 with standing cuff portion 17 of the cuff 14 being tacked down to the topsheet 12 by tackdown bond 52. In FIGS. 8A-B, the cuffs 14 are mechanically bonded to the backsheet poly 26 by an absorbent assembly bond 32 and a no-leak glue 45 and are secured to the backsheet 28 by an adhesive 30. FIG. 8A shows standing cuff portion 17 laterally offset from the longitudinal edge of the absorbent core 24 with elastic members 42, 44, 36, 38 located outboard of the assembly bond 32. FIG. 8B shows the construction at the side panel 48 with standing cuff portion 17 of the cuff 14 tacked down to the topsheet 12.

Figure 9:
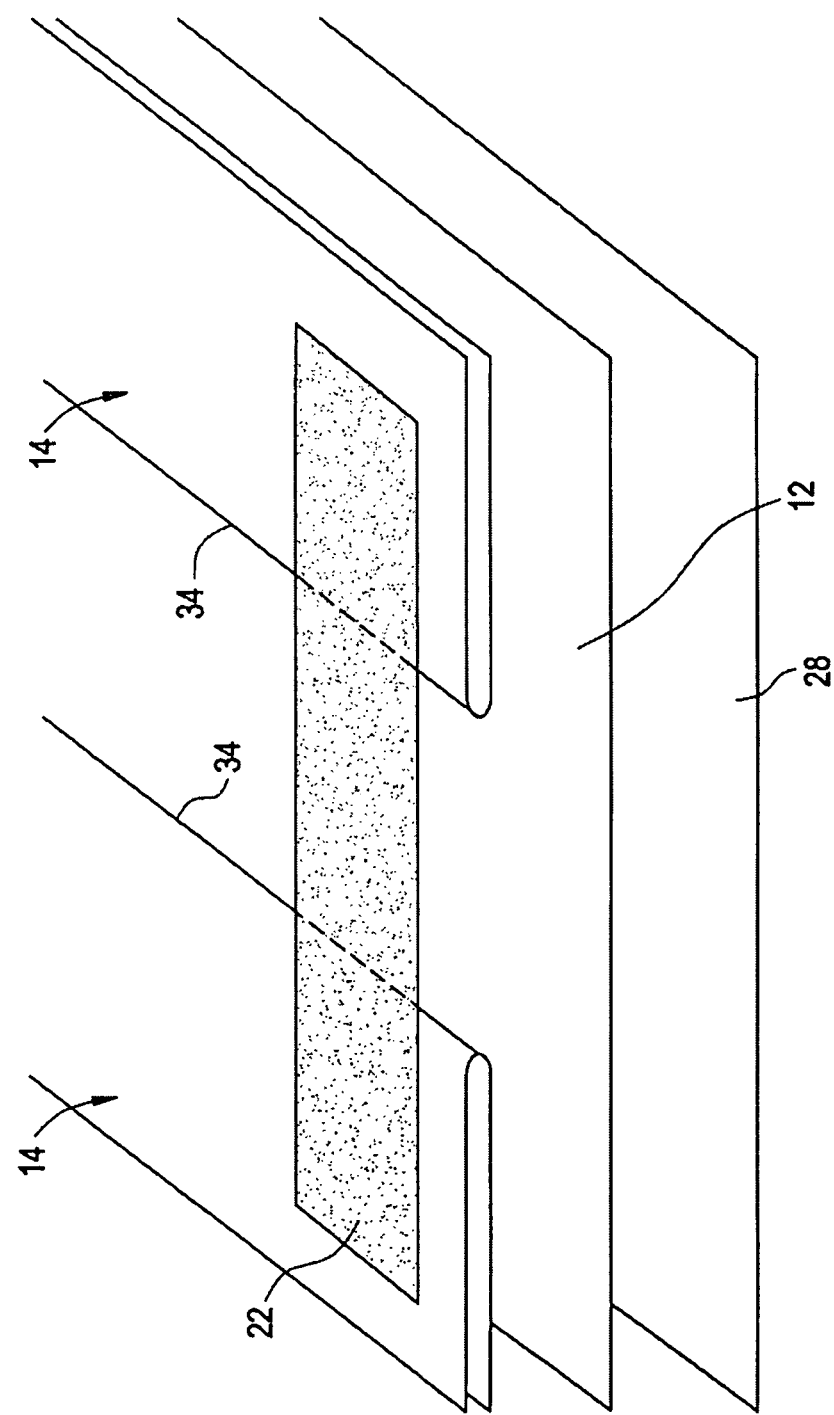
FIG. 9 is a perspective, exploded view of an end region of a diaper in accordance with an embodiment of the present invention.
Figure 10A:
FIG. 10A-E is a process flow diagram showing steps for assembling a diaper in accordance with one embodiment of the present invention.
Figure 10B:
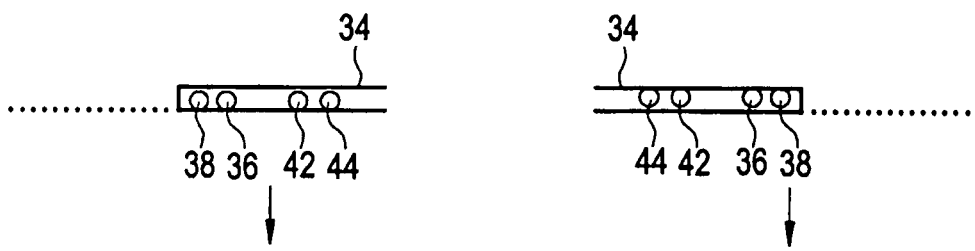
Figure 10C:
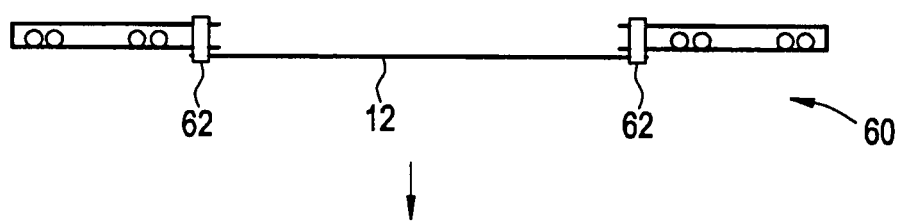
Figure 10D:
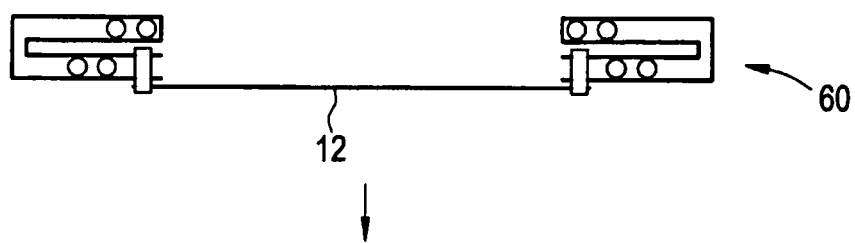
Figure 10E:
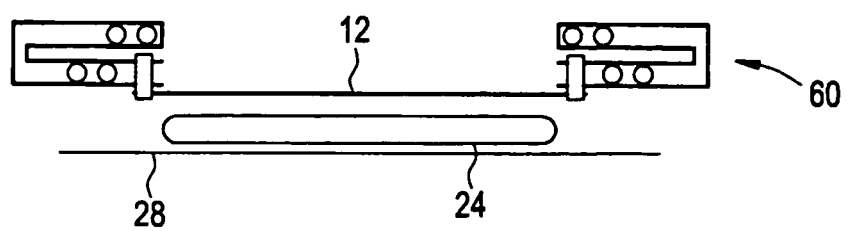

In certain embodiments, the elastically contractible cuffs 14 may be integrated with the waist band 22, 20 to form a continuous gasket around the periphery of the absorbent area, i.e., around the absorbent core. The folding of the cuff material to form the cuff according to one embodiment of the present invention creates pockets with waist features to form a 360 degree gasket. FIG. 9 shows one embodiment of a such a diaper construction, where the ends of the cuffs 14 are secured between the waistband 22 and the topsheet 12, which is in turn joined to backsheet 28.

Advantageously, the construction may include an absorbent waist feature, such as by printing or other placement of absorbent polymer onto the nonwoven material that forms the waistband. In this way, as the waistband swells it may create regosity that allows fluid to be trapped under it, thereby preventing leakage, especially on subsequent loading of liquid exudate with slower acquisition. The waistband 22 also may help hold up the barrier leg cuff near the waist of the wearer.

A diaper having the elastically contractible cuffs 14 described herein may be made as described in FIG. 10 or by using various combinations other cutting, folding, bond, and other techniques known in the art. In FIG. 10, the process, which preferably may be done in a continuous fashion, begins with formation of a pair of cuffs. In Step A, pre-strained elastic members 36, 38, 42, and 44 may be placed onto the continuous cuff material 34 and coated with an adhesive (not shown). Then, in Step B, the cuff material 34 may be folded to wrap the elastic members 36, 38, 42, and 44. In Step C, the cuff material with elastic members may be connected to a topsheet 12 by a cuff-topsheet bond 62, to form a cuff/topsheet composite 60. In Step D, the cuff material with elastic members may be folded, to form a bucket shape. Then the cuff/topsheet composite 60 may be combined with other components of a diaper, such as side panels, a backsheet, and an absorbent core. For example, in Step E, the cuff/topsheet composite 60 is secured together with an absorbent core 24 and a backsheet 28. In one embodiment, which is not shown, a waistband may be secured to the inner surface of the topsheet the cuffs, so as to connect the two cuffs about their ends to form a continuous gasket.

The diaper may also be provided with a closure system (also called a "fastening system") for fitting the diaper on the wearer. The closure system may take on a number of configurations such as adhesive tape tabs, mechanical closure tape tabs, fixed position fasteners, side seams as for training pants, or any other closure means as are known in the art. The closure system may include an adhesive tape tab fastening system including a pair of tape tab fastening members and a landing member, such as a reinforcing strip or, in the alternative, a portion of the backsheet, positioned in the front waist region of the diaper. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993.

In a certain embodiment, the disposable absorbent article is a disposable training pant with the offset elastically contractible cuffs described herein and with elastically extensible side panels for improved fit and comfort. Examples of constructing the side panels and chassis are described in U.S. Pat. No. 5,246,433 to Hasse et al. and in U.S. Pat. No. 5,591,155 to Nishikawa et al.

Figure 11:
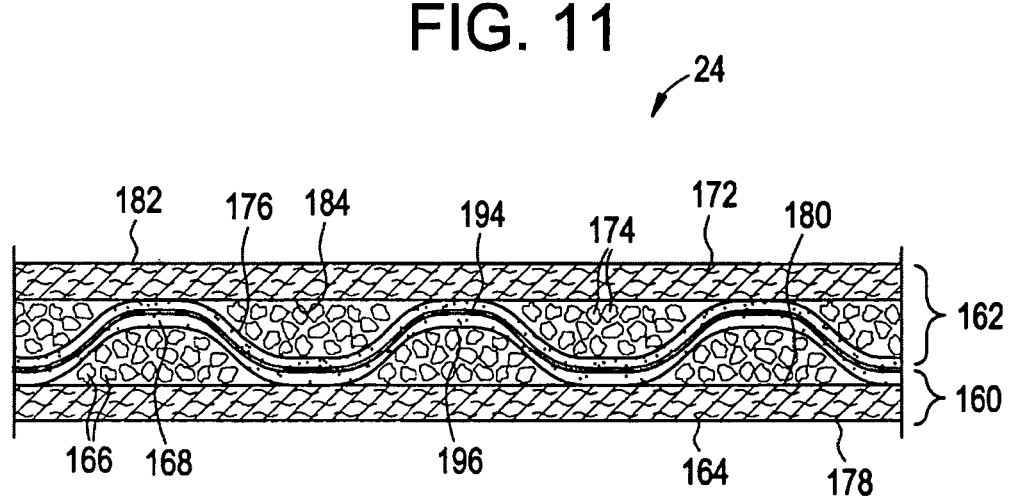
FIG. 11 is a partial cross-sectional view of an absorbent core layer in accordance with an embodiment of this invention.

The absorbent core 24 generally is disposed between the topsheet 12 and the backsheet 28 and may comprises two layers, a first absorbent layer 160 and a second absorbent layer 162. As best shown in FIG. 11, the first absorbent layer 160 of the absorbent core 24 comprises a substrate 164, an absorbent particular polymer material 166 on the substrate 164, and a thermoplastic composition 168 on the absorbent particulate polymer material 166 and at least portions of the first substrate 164 as an adhesive for covering and immobilizing the absorbent particulate polymer material 166 on the first substrate 164. According to another embodiment, the first absorbent layer 160 of the absorbent core 24 may also include a cover layer (not shown) on the thermoplastic composition 168. The second absorbent layer 162 of the absorbent core 24 may also include a substrate 172, an absorbent particulate polymer material 174 on the second substrate 172, and a thermoplastic composition 176 on the absorbent particulate polymer material 74 and at least a portion of the second substrate 172 for immobilizing the absorbent particulate polymer material 174 on the second substrate 172. Although not illustrated, the second absorbent layer 162 may also include a cover layer.

The substrate 164 of the first absorbent layer 160 may be referred to as a dusting layer and has a first surface 178 which faces the backsheet 28 of the diaper 10 and a second surface 180 which faces the absorbent particulate polymer material 166. Likewise, the substrate 172 of the second absorbent layer 162 may be referred to as a core cover and has a first surface 182 facing the topsheet 12 of the diaper 10 and a second surface 184 facing the absorbent particulate polymer material 174. The first and second substrates 164 and 172 may be adhered to one another with adhesive about the periphery to form an envelope about the absorbent particulate polymer materials 166 and 174 to hold the absorbent particulate polymer material 166 and 174 within the absorbent core 24.

According to a certain embodiment, the substrates 164 and 172 of the first and second absorbent layers 160 and 162 may be a non-woven material, such as those nonwoven materials described above. In certain embodiments, the nonwovens are porous and in one embodiment has a pore size of about 32 microns.

The absorbent particulate polymer material 166 and 174 is deposited on the respective substrates 164 and 172 of the first and second absorbent layers 160 and 162 in clusters of particles to form a grid pattern comprising land areas 194 and junction areas 196 between the land areas 194. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 196 in the grid pattern contain little or no absorbent particulate polymer material 166 and 174. The land areas 194 and junction areas 196 can have a variety of shapes including, but not limited to, circular, oval, square, rectangular, triangular, and the like.

The grid pattern of absorbent particulate polymer material clusters is arranged on the substrates 164 and 172 of the respective absorbent layers 160 and 162 such that the grid pattern formed by the arrangement of land areas 194 and junction areas 196 forms a pattern angle. The pattern angle may be 0, greater than 0, or 15 to 30 degrees, or from about 5 to about 85 degrees, or from about 10 to about 60 degrees, or from about 15 to about 30 degrees.

The first and second layers 160 and 162 may be combined to form the absorbent core 24. The absorbent core 24 has an absorbent particulate polymer material area extending bounded by a pattern length and a pattern width. The extent and shape of the absorbent particulate polymer material area may vary depending on the desired application of the absorbent core 24 and the particular absorbent article in which it may be incorporated. In a certain embodiment, however, the absorbent particulate polymer material area extends substantially entirely across the absorbent core 24.

The first and second absorbent layers 160 and 162 may be combined together to form the absorbent core 14 such that the grid patterns of the respective first and second absorbent layers 162 and 164 are offset from one another along the length and/or width of the absorbent core 24. The respective grid patterns may be offset such that the absorbent particulate polymer material 166 and 174 is substantially continuously distributed across the absorbent particulate polymer area. In a certain embodiment, absorbent particulate polymer material 166 and 174 is substantially continuously distributed across the absorbent particulate polymer material area despite the individual grid patterns comprising absorbent particulate polymer material 166 and 174 discontinuously distributed across the first and second substrates 164 and 172 in clusters. In a certain embodiment, the grid patterns may be offset such that the land areas 194 of the first absorbent layer 160 face the junction areas of the second absorbent layer 162 and the land areas 194 of the second absorbent layer 162 face the junction areas of the first absorbent layer 160. When the land areas 194 and junction areas 196 are appropriately sized and arranged, the resulting combination of absorbent particulate polymer material 166 and 174 is a substantially continuous layer of absorbent particular polymer material across the absorbent particulate polymer material area of the absorbent core 24 (i.e. first and second substrates do not form a plurality of pockets, each containing a cluster of absorbent particulate polymer material therebetween). In a certain embodiment, respective grid patterns of the first and second absorbent layer 160 and 162 may be substantially the same.

In a certain embodiment, the amount of absorbent particulate polymer material 166 and 174 may vary along the length of the grid pattern. In a certain embodiment, the grid pattern may be divided into a number of absorbent zones, in which the amount of absorbent particulate polymer material 166 and 174 varies from zone to zone. As used herein, "absorbent zone" refers to a region of the absorbent particulate polymer material area having boundaries that are perpendicular to the longitudinal axis. The amount of absorbent particulate polymer material 166 and 174 may, in a certain embodiment, gradually transition from one of the plurality of absorbent zones to another. This gradual transition in amount of absorbent particulate polymer material 166 and 174 may reduce the possibility of cracks forming in the absorbent core 24.

The amount of absorbent particulate polymer material 166 and 174 present in the absorbent core 24 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 24 consists essentially of the first and second substrates 164 and 172, the absorbent particulate polymer material 166 and 174, and the thermoplastic adhesive composition 168 and 176. In an embodiment, the absorbent core 24 may be substantially cellulose free.

According to certain embodiments, the weight of absorbent particulate polymer material in at least one freely selected first square measuring 1 cm×1 cm may be at least about 10%, or 20%, or 30%, 40% or 50% higher than the weight of absorbent particulate polymer material in at least one freely selected second square measuring 1 cm×1 cm. In a certain embodiment, the first and the second square are centered about the longitudinal axis.

The absorbent particulate polymer material area may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article which is less than about 100 mm, 90 mm, 80 mm, 70 mm, 60 mm, or even less than about 50 mm.

It has been found that, for most absorbent articles such as diapers, the liquid discharge occurs predominately in the front half of the diaper. The front half of the absorbent core 24 should therefore comprise most of the absorbent capacity of the core. Thus, according to certain embodiments, the front half of said absorbent core 24 may comprise more than about 60% of the superabsorbent material, or more than about 65%, 70%, 75%, 80%, 85%, or 90% of the superabsorbent material.

In certain embodiments, the absorbent core 24 may further comprise any absorbent material that is generally compressible, conformable, non-irritating to the wearer's skin, and capable of absorbing and retaining liquids such as urine and other certain body exudates. In such embodiments, the absorbent core 24 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 24 may further comprise minor amounts (typically less than about 10%) materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The thermoplastic adhesive material 168 and 176 may serve to cover and at least partially immobilize the absorbent particulate polymer material 166 and 174. In one embodiment of the present invention, the thermoplastic adhesive material 168 and 176 may be disposed essentially uniformly within the absorbent particulate polymer material 166 and 174, between the polymers. However, in a certain embodiment, the thermoplastic adhesive material 168 and 176 may be provided as a fibrous layer which is at least partially in contact with the absorbent particulate polymer material 166 and 174 and partially in contact with the substrate layers 164 and 172 of the first and second absorbent layers 160 and 162. In one embodiment, the absorbent particulate polymer material 166 and 174 may be provided as a discontinuous layer, and a layer of fibrous thermoplastic adhesive material 168 and 176 is laid down onto the layer of absorbent particulate polymer material 166 and 174, such that the thermoplastic adhesive material 168 and 176 is in direct contact with the absorbent particulate polymer material 166 and 174, but also in direct contact with the second surfaces 180 and 184 of the substrates 164 and 172, where the substrates are not covered by the absorbent particulate polymer material 166 and 174. This imparts an essentially three-dimensional structure to the fibrous layer of thermoplastic adhesive material 168 and 176, which in itself is essentially a two-dimensional structure of relatively small thickness, as compared to the dimension in length and width directions. In other words, the thermoplastic adhesive material 168 and 176 undulates between the absorbent particulate polymer material 168 and 176 and the second surfaces of the substrates 164 and 172.

Thereby, the thermoplastic adhesive material 168 and 176 may provide cavities to cover the absorbent particulate polymer material 166 and 174, and thereby immobilizes this material. In a further aspect, the thermoplastic adhesive material 168 and 176 bonds to the substrates 164 and 172 and thus affixes the absorbent particulate polymer material 166 and 174 to the substrates 164 and 172. Thus, in accordance with certain embodiments, the thermoplastic adhesive material 168 and 176 immobilizes the absorbent particulate polymer material 166 and 174 when wet, such that the absorbent core 24 achieves an absorbent particulate polymer material loss of no more than about 70%, 60%, 50%, 40%, 30%, 20%, 10%, according to the Wet Immobilization Test described herein. Some thermoplastic adhesive materials will also penetrate into both the absorbent particulate polymer material 166 and 174 and the substrates 164 and 172, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 24 is dry. The thermoplastic adhesive material may also be referred to as a hot melt adhesive.

Without wishing to be bound by theory, it has been found that those thermoplastic adhesive materials which are most useful for immobilizing the absorbent particulate polymer material 166 and 174 combine good cohesion and good adhesion behavior. Good adhesion may promote good contact between the thermoplastic adhesive material 168 and 176 and the absorbent particulate polymer material 166 and 174 and the substrates 164 and 172. Good cohesion reduces the likelihood that the adhesive breaks, in particular in response to external forces, and namely in response to strain. When the absorbent core 24 absorbs liquid, the absorbent particulate polymer material 166 and 174 swells and subjects the thermoplastic adhesive material 168 and 176 to external forces. In certain embodiments, the thermoplastic adhesive material 168 and 176 may allow for such swelling, without breaking and without imparting too many compressive forces, which would restrain the absorbent particulate polymer material 166 and 174 from swelling.

In accordance with certain embodiments, the thermoplastic adhesive material 168 and 176 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $6\,°C<T_g<16°$ C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 168 and 176 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material 168 and 176 to the substrates 164 and 172 or to any other layer, in particular any other nonwoven layer, such layers may be pre-treated with an auxiliary adhesive.

In certain embodiments, the thermoplastic adhesive material 168 and 176 will meet at least one, or several, or all of the following parameters:

An exemplary thermoplastic adhesive material 168 and 176 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more than 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

The absorbent core 24 may also comprise an auxiliary adhesive which is not illustrated in the figures. The auxiliary adhesive may be deposited on the first and second substrates 164 and 172 of the respective first and second absorbent layers 160 and 162 before application of the absorbent particulate polymer material 166 and 174 for enhancing adhesion of the absorbent particulate polymer materials 166 and 174 and the thermoplastic adhesive material 168 and 176 to the respective substrates 164 and 172. The auxiliary glue may also aid in immobilizing the absorbent particulate polymer material 166 and 174 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates by any suitable means, but according to certain embodiments, may be applied in about 0.5 mm to about 1 mm wide slots spaced about 0.5 mm to about 2 mm apart.

The cover layer may comprise the same material as the substrates 164 and 172, or may comprise a different material. In certain embodiments, suitable materials for the cover layer are the nonwoven materials, typically the materials described above as useful for the substrates 164 and 172.

The diaper may further comprise an acquisition system (not shown) disposed between the liquid permeable topsheet 12 and a wearer facing side of the absorbent core 24. The acquisition system may be in direct contact with the absorbent core. The acquisition system may comprise a single layer or multiple layers, such as an upper acquisition layer facing towards the wearer's skin and a lower acquisition layer facing the garment of the wearer. According to a certain embodiment, the acquisition system may function to receive a surge of liquid, such as a gush of urine. In other words, the acquisition system may serve as a temporary reservoir for liquid until the absorbent core 24 can absorb the liquid.

In a certain embodiment, the acquisition system may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on a glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers may comprise a non-woven, which may be hydrophilic. Further, according to a certain embodiment, one or both of the upper and lower acquisition layers may comprise the chemically cross-linked cellulosic fibers, which may or may not form part of a nonwoven material. According to an exemplary embodiment, the upper acquisition layer may comprise a nonwoven, without the cross-linked cellulosic fibers, and the lower acquisition layer may comprise the chemically cross-linked cellulosic fibers. Further, according to an embodiment, the lower acquisition layer may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer has a total dry weight, the cross-linked cellulosic fibers are present on a dry weight basis in the upper acquisition layer in an amount from about 30% to about 95% by weight of the lower acquisition layer, and the other natural or synthetic polymeric fibers are present on a dry weight basis in the lower acquisition layer in an amount from about 70% to about 5% by weight of the lower acquisition layer. According to another embodiment, the cross-linked cellulosic fibers are present on a dry weight basis in the first acquisition layer in an amount from about 80% to about 90% by weight of the lower acquisition layer, and the other natural or synthetic polymeric fibers are present on a dry weight basis in the lower acquisition layer in an amount from about 20% to about 10% by weight of the lower acquisition layer.

According to a certain embodiment, the lower acquisition layer desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer has a maximum uptake of about 10 g/g.

A relevant attribute of the upper acquisition layer is its Median Desorption Pressure, MDP. The MDP is a measure of the capillary pressure that is required to dewater the lower acquisition layer to about 50% of its capacity at 0 cm capillary suction height under an applied mechanical pressure of 0.3 psi. Generally, a relatively lower MDP may be useful. The lower MDP may allow the lower acquisition layer to more efficiently drain the upper acquisition material. Without wishing to be bound by theory, a given distribution material may have a definable capillary suction. The ability of the lower acquisition layer to move liquid vertically via capillary forces will be directly impacted by gravity and the opposing capillary forces associated with desorption of the upper acquisition layer. Minimizing these capillary forces may positively impact the performance of the lower acquisition layer. However, in a certain embodiment the lower acquisition layer may also have adequate capillary absorption suction in order to drain the layers above (upper acquisition layer and topsheet 12, in particular) and to temporarily hold liquid until the liquid can be partitioned away by the absorbent core components. Therefore, in a certain embodiment, the lower acquisition layer may have a minimum MDP of greater than 5 cm. Further, according to exemplary embodiments, the lower acquisition layer has an MDP value of less than about 20.5 cm $H_2O$, or less than about 19 cm $H_2O$, or less than about 18 cm $H_2O$ to provide for fast acquisition.

The methods for determining MDP, and maximum uptake are disclosed in U.S. patent application Ser. No. 11/600,691 (Flohr et al.). For example, according to a first embodiment, the lower acquisition layer may comprise about 70% by weight of chemically cross-linked cellulose fibers, about 10% by weight polyester (PET), and about 20% by weight untreated pulp fibers. According to a second embodiment, the lower acquisition layer may comprise about 70% by weight chemically cross-linked cellulose fibers, about 20% by weight lyocell fibers, and about 10% by weight PET fibers. According to a third embodiment, the lower acquisition layer may comprise about 68% by weight chemically cross-linked cellulose fibers, about 16% by weight untreated pulp fibers, and about 16% by weight PET fibers. In one embodiment, the lower acquisition layer may comprise from about 90% to about 100% by weight chemically cross-linked cellulose fibers.

Suitable non-woven materials for the upper and lower acquisition layers include, but are not limited to SMS material, comprising a spunbonded, a melt-blown and a further spunbonded layer. In certain embodiments, permanently hydrophilic nonwovens, and in particular, nonwovens with durably hydrophilic coatings are desirable. Another suitable embodiment comprises a SMMS-structure. In certain embodiments, the nonwovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S.

Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in the co-pending patent application Ser. No. 10/758,066 entitled "Disposable absorbent article comprising a durable hydrophilic core wrap" to Ekaterina Anatolyevna Ponomarenko and Mattias NMN Schmidt.

Further useful nonwovens are described in U.S. Pat. No. 6,645,569 to Cramer et al., U.S. Pat. No. 6,863,933 to Cramer et al., U.S. Pat. No. 7,112,621 to Rohrbaugh et al., and co-pending U.S. patent application Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic nonwovens are also useful in other parts of an absorbent article. For example, topsheets and absorbent core layers comprising permanently hydrophilic nonwovens as described above have been found to work well.

According to a certain embodiment, the upper acquisition layer may comprise a material that provides good recovery when external pressure is applied and removed. Further, according to a certain embodiment, the upper acquisition layer may comprise a blend of different fibers selected, for example from the types of polymeric fibers described above. In some embodiments, at least a portion of the fibers may exhibit a spiral-crimp which has a helical shape. In some embodiments, the upper acquisition layer may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio). The test method and apparatuses described below may be useful in testing embodiments of this invention:

Wet Immobilization Test

Equipment
  Graduated Cylinder
  Stop watch (±0.1 sec)
  Scissors
  Light Box
  Pen
  Test solution: 0.90% saline solution at 37° C.
  Metal ruler traceable to NIST, DIN, JIS or other comparable National Standard
  PVC/metal dishes with a flat surface inside and a minimum length of the core bag length (n) to be measured and a maximum length n+30 mm, width of 105±5 mm, height of 30-80 mm or equivalent
  Electronic Force Gauge (Range 0 to 50 Kg)
  Wet Immobilization Impact Tester Equipment (WAIIT), Design package number: BM-00112.59500-R01 available from T.M.G. Technisches Buero Manfred Gruna Facilities:
  Standard laboratory conditions, temperature: 23° C.±2° C., relative humidity: <55%

Sample Preparation
  1. Open the product, topsheet side up.
  2. Unfold the diaper and cut the cuff elastics approximately every 2.5 cm to avoid chassis tension.
  3. For pull-up products open the side seams and remove the waistbands.
  4. Lay the core bag flat and rectangular topsheet side up onto the light box surface without any folds.
  5. Switch on the light box to clearly identify the absorbent core outer edges.
  6. With a ruler, draw a line at the front and back absorbent core outer edges.
  7. Measure the distance (A), between the two markers and divide the value by 2, this will be calculated distance (B).
  8. Measure the calculated distance (B) from front marker towards the middle of the core bag and mark it. At this marker draw a line in the cross direction.

Test Procedure

WAIIT Calibration:
  1. Make sure that the sliding board is in the lower position. Open the front door of the WAIIT tester and connect the force gauge hook to the upper sample clamp of the WAIIT. Make sure that the clamp is closed before connecting the spring-balance.
  2. Use both hands on the spring-balance to lift continuously and as slowly as possible up the sliding board towards the upper position. Record the average value ($m_1$) during the execution to the nearest 0.02 kg.
  3. Guide down the sliding board as slowly as possible to the lower position and record the average value ($m_2$) read off during execution to the nearest 0.02 kg.
  4. Calculate and report the delta of $m_1-m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:

Drop height is 50 cm.

Diaper load ($I_D$) is 73% of the core capacity (cc); $I_D=0.73\times cc$.

Core capacity (cc) is calculated as: $cc=m_{SAP}\times SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test Execution:

1. Reset the balance to zero (tare), put the dry core bag on the balance, weigh and report it to the nearest 0.1 g.
2. Measure the appropriate volume Saline (0.9% NaCl in deionized water) with the graduated cylinder.
3. Lay the core bag, topsheet side up, flat into the PVC dish. Pour the saline evenly over the core bag.
4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (±1 minute) to allow all saline to be absorbed. Some drops may retain in the PVC dish. Use only the defined PVC/metal dish to guarantee homogenous liquid distribution and less retained liquid.
5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking. Otherwise scrap the pad and use the next one.
6. Take the loaded core bag and cut the pad along the marked line in the cross direction.
7. Put the back of the wet core bag onto the balance ($m_1$). Weigh and report it to the nearest 0.1 g.
8. Take the wet core and clamp the end seal side in the top clamp of the sample holder of the WAIIT (open end of the core oriented down). Next, clamp both sides of the core with the side clamps of the sample holder making sure that the product is fixed to the sample holder along the whole product length. Make sure not to clamp the absorbent core, only the nonwoven; for some products this means securing the product with only the barrier leg cuff.
9. Lift up the sliding board to the upper position by using both hands until the board is engaged.
10. Close the safety front door and release the slide blade.
11. Reset the balance to zero (tare), take the tested core bag out of the WAIIT and put it on the balance ($m_2$). Report the weight to the nearest 0.1 g.
12. Repeat steps 7 to 11 with front of the wet core bag.

Reporting:

1. Record the dry core bag weight to the nearest 0.1 g.
2. Record the wet weight before ($m_{1\ front/back}$) and after ($m_{2\ front/back}$) testing, both to the nearest 0.1 g.
3. Calculate and report the average weight loss ($\Delta m$) to the nearest 0.1 g: $\Delta m=(m_{1front}+M_{1back})-(m_{2front}+m_{2back})$
4. Calculate and report the weight loss in percent to the nearest 1%, ($\Delta m_{rel}$): $(\Delta m_{rel})=(((m_{1front}+m_{1back})-(m_{2front}+m_{2back}))\times 100)/(m_{1front}+m_{1back})$
5. Calculate and report Wet Immobilization (WI) as: $WI=100\%-\Delta m_{rel}$ All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
    an absorbent core having a garment surface and an opposed body surface, which surfaces meet along a pair of longitudinal edges and a pair of end edges;
    a liquid permeable topsheet positioned adjacent the body surface of the absorbent core and having a pair of opposed longitudinal edges;
    a liquid impermeable backsheet positioned adjacent the garment surface of the absorbent core; and
    a pair of elastically contractible cuffs, each of which is constructed of a continuous cuff material and has a standing cuff portion which comprises one or more elastic members,
    wherein each elastically contractible cuff is secured about one of said longitudinal edges of the topsheet by an assembly bond, with the standing cuff portion having a free edge and being laterally offset away from the longitudinal edge of the absorbent core; wherein the assembly bond is located outboard of the absorbent core and inboard of all of the elastic members of the standing cuff portion; wherein each cuff includes one or more cuff folds, a cuff fold bond, and a cuff end bond.

2. The disposable absorbent article of claim 1, wherein the elastically contractible cuff is attached to the topsheet.

3. The disposable absorbent article of claim 2, wherein the elastically contractible cuff is mechanically bonded to the topsheet or glued to the backsheet.

4. The disposable absorbent article of claim 1, wherein the elastically contractible cuff is attached to the backsheet.

5. The disposable absorbent article of claim 1, wherein the standing cuff portion comprises at least two layers of the continuous cuff material.

6. The disposable absorbent article of claim 5, wherein two or more of the elastic members are disposed between the at least two layers of the continuous cuff material, wherein one or more of the elastic members are fixed to the continuous cuff material by intermittent adhesive zones, wherein the adhesive zones comprise at least two discrete sections along the length of the elastic member.

7. The disposable absorbent article of claim 1, wherein the standing cuff portion comprises at least three layers of the continuous cuff material.

8. The disposable absorbent article of claim 1, wherein the continuous cuff material comprises a proximate end region and a distal end region, and both of the end regions are bonded together with the assembly bond.

9. The disposable absorbent article of claim 1, wherein the absorbent core comprises an absorbent particulate polymer material and which is substantially cellulose free.

10. The disposable absorbent article of claim 1, further comprising a pair of waistbands located, along opposing end edges of the topsheet.

11. The disposable absorbent article of claim 10 wherein the pair of elastically contractible cuffs are connected with the pair of waistbands to form a continuous gasket around the periphery of the absorbent core.

12. The disposable absorbent article of claim 1, further comprising a pair of side panels.

13. The disposable absorbent article of claim 12 wherein the absorbent article is a diaper and the pair of side panels comprise a re-closable fastening system for securing the diaper to a wearer.

14. The disposable absorbent article of claim 12 wherein the absorbent article is a pant-type diaper and the pair of side panels are joined to each other to form a pant.

15. The disposable absorbent article of claim 1, wherein the standing cuff portion is folded so that the distal edge of the standing cuff portion is pointing outboard of the absorbent article.

16. The disposable absorbent article of claim 1, wherein at least a portion of the contractible cuff is constructed of a single layer of a continuous cuff material.

17. A disposable absorbent article comprising:
an absorbent core having a garment surface and an opposed body surface, which surfaces meet along a pair of longitudinal edges and a pair of end edges, wherein the absorbent core comprises an absorbent particulate polymer material and which is substantially cellulose free;
a liquid permeable topsheet positioned adjacent the body surface of the absorbent core and having a pair of opposed longitudinal edges and a pair of opposed end edges;
a liquid impermeable backsheet positioned adjacent the garment surface of the absorbent core;
a pair of elastically contractible cuffs, each of which is constructed of a continuous cuff material and has a standing cuff portion which comprises from two to four elastic members, wherein each elastically contractible cuff is secured about one of said longitudinal edges of the topsheet by an assembly bond, with the standing cuff portion having a free edge and being laterally offset away from the longitudinal edge of the absorbent core; wherein the assembly bond is located outboard of the absorbent core and inboard of all of the elastic members of the standing cuff portion; wherein each cuff includes one or more cuff folds, a cuff fold bond, and a cuff end bond; and
a pair of unitary waistbands connected to the pair of elastically contractible cuffs to form a continuous gasket around the periphery of the absorbent core area, wherein the elastically contractible cuff is mechanically bonded to the topsheet and glued to the backsheet.

* * * * *